(12) United States Patent
Docherty et al.

(10) Patent No.: US 6,867,330 B2
(45) Date of Patent: Mar. 15, 2005

(54) HALOGENATED PHOSPHINES

(75) Inventors: Gordon Findlay Docherty, Birmingham (GB); Floryan De Campo, Mount Pleasant, SC (US)

(73) Assignee: Rhodia Consumer Specialties Limited, Watford (GB)

( * ) Notice: Subject to any disclaimer, the term of this patent is extended or adjusted under 35 U.S.C. 154(b) by 0 days.

(21) Appl. No.: 10/468,493

(22) PCT Filed: Feb. 27, 2002

(86) PCT No.: PCT/GB02/00853
§ 371 (c)(1), (2), (4) Date: Oct. 1, 2003

(87) PCT Pub. No.: WO02/070530
PCT Pub. Date: Sep. 12, 2002

(65) Prior Publication Data
US 2004/0106816 A1 Jun. 3, 2004

(30) Foreign Application Priority Data
Mar. 1, 2001 (GB) .............................. 0105053

(51) Int. Cl.$^7$ ................................................ C07F 9/02
(52) U.S. Cl. ............................ 568/8; 562/808; 562/820
(58) Field of Search ................................ 562/808, 820; 568/8

(56) References Cited

U.S. PATENT DOCUMENTS

| | | | | | |
|---|---|---|---|---|---|
| 3,078,304 A | * | 2/1963 | Niebergall | ................... | 562/820 |
| 3,734,958 A | * | 5/1973 | Rio | ............................ | 562/820 |
| 3,755,460 A | * | 8/1973 | Staendeke | ...................... | 568/8 |
| 4,521,346 A | * | 6/1985 | Kleiner | ........................ | 562/820 |
| 4,752,648 A | | 6/1988 | Weferling et al. | | |

FOREIGN PATENT DOCUMENTS

| | | |
|---|---|---|
| EP | 1 070 723 A | 1/2001 |
| GB | 1 031 839 A | 6/1966 |

OTHER PUBLICATIONS

CA:121:230878 abs of Phosphorus, Sulfur and Silicon and Related elements by Goerlich et al 88(1–4) pp 241–4 1994.*
Majewski P.: "Investigation of the reaction between dialkylphosphines and carbon tetrachloride. Part I" Phosphorus, Sulfur and Silicon and the Related Elements, vol. 85, No. 1–4, 1993, pp. 41–47, XP008003002 Gordon and Breach Science Publishers, Amsterdam, GB ISSN: 1042–6507.

* cited by examiner

*Primary Examiner*—Deborah D. Carr
(74) *Attorney, Agent, or Firm*—Frishauf, Holtz, Goodman & Chick, P.C.

(57) ABSTRACT

Halogenated phosphines are produced by reacting a secondary phosphine with a quaternary phosphonium halide, in a solvent/carrier for the reactants.

12 Claims, No Drawings

HALOGENATED PHOSPHINES

This application is a U.S. National Phase Application under 35 USC 371 of International Application PCT/GB02/00853 (published in English) filed Feb. 27, 2002.

This invention relates to halogenated phosphines and in particular to a method for the production of halogenated phosphines and to halogenated phosphines obtained thereby.

U.S. Pat. No. 4,752,648 discloses a method of making halogenated phosphines by reacting a secondary phosphine, either with phosphorus pentachloride or with phosphorus trichloride and elemental chlorine. The said U.S. Patent also discloses that the use of phosphorus trichloride in the reaction can lead to the production of " . . . insoluble . . . red-orange solid matter" which requires removal from the reaction mixture in order to isolate the desired product.

We have now unexpectedly found that the said "solid matter", which is believed to consist essentially of a quaternary phosphonium halide, can be reacted with a secondary phosphine to produce a halogenated phosphine, in an acceptably high yield and state of purity. Effectively, a material which has hitherto been regarded as an undesirable by-product is used, in accordance with the present invention, as a reactant.

Accordingly, the present invention provides a method for the production of a halogenated phosphine by reacting a secondary phosphine with a halogen source, in which said halogen source comprises a quaternary phosphonium halide.

The present invention also provides a halogenated phosphine produced by the method described in the immediately-preceding paragraph.

In accordance with the present invention, the secondary phosphine may conveniently be represented by the general formula (I):

$R_1R_2PH$                (I)

in which each of $R_1$ and $R_2$ (which may be the same or different) denotes an alkyl, aryl, aralkyl, alkaryl or cycloalkyl group.

Further in accordance with the present invention, the quaternary phosphonium halide may conveniently be represented by the general formula (II):

$[R_3R_4X_2P]^+X^-$           (II)

in which each of $R_3$ and $R_4$ (which may be the same or different relative to each other and to $R_1$ and $R_2$) likewise denotes an alkyl, aryl, aralkyl, alkaryl or cycloalkyl group and X denotes a halogen.

For example, $R_1$, $R_2$, $R_3$, and $R_4$ may each independently be selected from $C_1$ to $C_4$ alkyl, phenyl, tolyl, xylyl and $C_5$ to $C_8$ cycloalkyl.

X may be chlorine, bromine or iodine, but preferably X is chlorine.

Preferably $R_1$, $R_2$, $R_3$ and $R_4$ are each cyclohexyl.

Thus, the preferred secondary phosphine in accordance with general formula (I) is di-cyclohexyl-phosphine. Similarly, the preferred quaternary phosphonium halide in accordance with general formula (II) is di-cyclohexyl-dichloro phosphonium chloride.

The reaction in accordance with the present invention is preferably carried out in an inert, non-polar liquid medium which acts as a solvent (or carrier) for the reactants. Examples of suitable liquid media include alkanes, haloalkanes, aralkanes and ethers. Preferred liquid media include toluene and chlorobenzene.

Preferably, the reaction according to the present invention is carried out under an inert atmosphere (e.g. argon).

The secondary phosphine and quaternary phosphonium halide should preferably be reacted in a molar ratio of about 1:1.

The present invention will be illustrated, merely by way of example, as follows:

1. EQUIPMENT

The equipment used is the same for both of the following reactions and comprises a 200 ml, 3-neck flask fitted with a reflux condenser, a stirrer bar, a dropping funnel (without a pressure equalising sidearm), a temperature probe and an argon inlet connected to a manifold. All the equipment is carefully dried before use and the reactions are carried out under argon at each stage.

2. EXAMPLE 1A

Preparation of Quaternary Phosphonium Halide

Phosphorus pentachloride (9.3 g, 0.0424 mole) was weighed into the flask and suspended in toluene (40 ml). The suspension was blanketed with argon. A solution of di-cyclohexyl phosphine (8.0 g, 0.040 mole) in toluene (40 ml) was placed in the dropping funnel.

The solution of di-cyclohexyl phosphine was added dropwise to the suspension of phosphorus pentachloride, keeping the temperature of the mixture between 15° C. and 30° C. On completion of the addition, the mixture was heated to 70–80° C. for one hour before being cooled to room temperature.

An orange precipitate (which had appeared on cooling of the mixture) was allowed to settle for 30 minutes. The supernatant liquid was then removed, by means of a filter cannula.

The precipitate was washed with toluene and vacuum-dried. Analysis of the resulting solid showed it to consist essentially of di-cyclohexyl-dichloro phosphonium chloride.

3. EXAMPLE 1B

Preparation of Halogenated Phosphine

Di-cyclohexyl-dichloro phosphonium chloride obtained as described in EXAMPLE 1A above (4.1 g, 0.0110 mole) was weighed into the flask and suspended in toluene (40 ml). The suspension was blanketed with argon. A solution of di-cyclohexyl phosphine (2.3 g, 0.0115 mole) in toluene (20 ml) was placed in the dropping funnel.

The solution of di-cyclohexyl phosphine was added dropwise to the suspension of the quaternary phosphonium chloride. The addition was carried out at room temperature and was observed to be slightly exothermic, although by the end of the addition the temperature had not exceeded 25° C.

On completion of the addition, the mixture was heated to 110–112° C. for 4 hours. Analysis of the mixture after that time showed that the quaternary phosphonium halide had been substantially completely consumed.

On cooling to room temperature, any precipitate was removed and the remaining clear solution was stripped of low-boiling components by heating at 60° C. and 15 mm Hg.

Analysis of the resulting oil showed it to comprise more than 84% di-cyclohexyl chlorophosphine. The weight of oil obtained (5.4 g) corresponded to a yield of about 90% of theoretical.

What is claimed is:

1. A method for the production of a halogenated phosphine by reacting a secondary phosphine with a halogen source, in which the halogen source is a quaternary phosphonium halide and wherein the secondary phosphine has the formula (I):

$R_1R_2PH$                (I)

where each of said $R_1$ and $R_2$ (which may be the same or different) denotes an alkyl, aryl, aralkyl, alkaryl or cycloalkyl group and wherein the quaternary phosphonium halide has the formula (II):

$$[R_3 R_4 X_2 P]^+ X^- \qquad (II)$$

where each of said $R_3$ and $R_4$ (which may be the same or different relative to each other and to $R_1$ and $R_2$) denotes an alkyl, aryl, aralkyl, alkaryl or cycloalkyl group and X denotes a halogen.

2. A method according to claim 1, in which $R_1$, $R_2$, $R_3$ and $R_4$ are each independently selected from the group consisting of $C_1$ to $C_4$ alkyl, phenyl, tolyl, xylyl and $C_5$ to $C_8$ cycloalkyl.

3. A method according to claim 1, in which the halogen source is a quaternary phosphonium chloride.

4. A method according to claim 1, in which the halogen source is a quaternary phosphonium bromide or iodide.

5. A method according to claim 1, in which $R_1$, $R_2$, $R_3$ and $R_4$ are each cyclohexyl.

6. A method according to claim 3, in which the secondary phosphine is di-cyclohexyl phosphine.

7. A method according to claim 1, in which the quaternary phosphonium halide is di-cyclohexyl-dichloro phosphonium chloride.

8. A method according to claim 1, in which the reaction is carried out in an inert, non-polar liquid medium selected from the group consisting of alkanes, haloalkanes, aralkanes and ethers.

9. A method according to claim 8, in which the liquid medium is toluene and chlororbenzene.

10. A method according to claim 1, in which the reaction is carried out under an inert atmosphere.

11. A method according to claim 10, in which the reaction is carried out under argon.

12. A method according to claim 1, in which the secondary phosphine and the quaternary phosphonium halide are reacted in a molar ratio of about 1:1.

* * * * *